(12) United States Patent
Suzuki et al.

(10) Patent No.: US 8,961,395 B2
(45) Date of Patent: Feb. 24, 2015

(54) TREATMENT DEVICE FOR ENDOSCOPE

(75) Inventors: Keita Suzuki, Tokyo (JP); Hideki Fujii, Tokyo (JP)

(73) Assignee: Olympus Medical Systems Corp. (JP)

( * ) Notice: Subject to any disclaimer, the term of this patent is extended or adjusted under 35 U.S.C. 154(b) by 853 days.

(21) Appl. No.: 12/967,177

(22) Filed: Dec. 14, 2010

(65) Prior Publication Data
US 2011/0178366 A1    Jul. 21, 2011

Related U.S. Application Data

(63) Continuation of application No. PCT/JP2010/003685, filed on Jun. 2, 2010.

(30) Foreign Application Priority Data

Jun. 15, 2009    (JP) ................. P2009-142115

(51) Int. Cl.
*A61B 1/00*       (2006.01)
*A61B 17/221*    (2006.01)
*A61B 18/14*     (2006.01)
(Continued)

(52) U.S. Cl.
CPC ............ *A61B 17/221* (2013.01); *A61B 18/14* (2013.01); *A61B 18/1445* (2013.01); *A61B 18/1492* (2013.01); *A61B 2017/00477* (2013.01); *A61B 2017/2212* (2013.01);
(Continued)

(58) Field of Classification Search
USPC .......... 600/104; 606/113, 114, 112, 127, 232
See application file for complete search history.

(56) References Cited

U.S. PATENT DOCUMENTS 5,667,525 A      9/1997  Ishibashi
6,077,274 A *   6/2000  Ouchi et al. ............... 606/113
(Continued)

FOREIGN PATENT DOCUMENTS

JP            46-4160       2/1971
JP            63-317149    12/1988
(Continued)

OTHER PUBLICATIONS

Int'l Search Report and English translation issued on related PCT/JP2010/003685 citing enclosed JP46-4160 offered as statement of relevancy in lieu of Abstract or translation.
(Continued)

*Primary Examiner* — Victor Nguyen
*Assistant Examiner* — Sarah Simpson
(74) *Attorney, Agent, or Firm* — Ostrolenk Faber LLP

(57) ABSTRACT

A treatment device for endoscope includes a flexible sheath, an operation wire that is advanceably/retreatably inserted into the sheath, a treatment part comprising at least one elastic wires that can enter and exit a tip side inner part of the sheath, and a connecting member that secures to each other a tip of the operation wire and ends of the elastic wires. The connecting member includes a cylindrical body part, and a plurality of walls that extend from one end face of the body part in the direction of the axis of the body unit. A proximal end of the operation wire is secured to the body part, and the plurality of ends of the elastic wires are secured to the wall in the direction of the axis; when viewed from the wall side in the direction of the axis, at least one of the ends of the elastic wires overlaps with the body part. The interval between mutually adjacent walls is narrower than the outer diameter of the elastic wires.

6 Claims, 9 Drawing Sheets

(51) Int. Cl.
*A61B 17/00* (2006.01)
*A61B 18/00* (2006.01)

(52) U.S. Cl.
CPC ................ *A61B 2017/2215* (2013.01); *A61B 2018/00214* (2013.01); *A61B 2018/1407* (2013.01)
USPC .......................................... 600/104; 606/113

(56) References Cited

U.S. PATENT DOCUMENTS

| | | | | |
|---|---|---|---|---|
| 6,090,129 | A * | 7/2000 | Ouchi | 606/206 |
| 7,387,632 | B2 * | 6/2008 | Ouchi | 606/47 |
| 8,118,819 | B2 * | 2/2012 | Miyamoto et al. | 606/139 |
| 8,157,811 | B2 * | 4/2012 | Shinozuka et al. | 606/113 |
| 2002/0133170 | A1 | 9/2002 | Tsuruta | |
| 2003/0114880 | A1 | 6/2003 | Hansen et al. | |
| 2003/0139750 | A1 * | 7/2003 | Shinozuka et al. | 606/113 |
| 2007/0288035 | A1 * | 12/2007 | Okada | 606/113 |
| 2008/0065156 | A1 * | 3/2008 | Hauser et al. | 606/232 |
| 2009/0112225 | A1 | 4/2009 | Kaneko et al. | |

FOREIGN PATENT DOCUMENTS

| | | |
|---|---|---|
| JP | 8-154944 | 6/1996 |
| JP | 10-179600 | 7/1998 |
| JP | 11-285500 | 10/1999 |
| JP | 2000-271146 | 10/2000 |
| JP | 2009-101153 | 5/2009 |

OTHER PUBLICATIONS

International Search Report and Written Opinion mailed Aug. 3, 2010 in corresponding PCT International Application No. PCT/JP2010/003685.

Search Report issued by European Patent Office and received by applicant on Sep. 19, 2012 in connection with corresponding EP patent application No. EP 10 78 9174.

* cited by examiner

US 8,961,395 B2

TREATMENT DEVICE FOR ENDOSCOPE

This application is a continuation application based on a PCT Patent Application No. PCT/JP2010/003685, filed Jun. 2, 2010. The contents of the PCT Application are incorporated herein by reference.

BACKGROUND OF THE INVENTION

1. Field of the Invention

The present invention relates to a treatment device for endoscope. More particularly, the present invention relates to a treatment device for endoscope that is used by advancing and retreating an operation wire inserted through a sheath.

2. Description of Related Art

Conventionally, treatment devices for endoscope of various configurations are used by insertion into a channel formed in an internal part of an endoscope. In one of these treatment devices for endoscope that is under consideration, an end part of a wire formed in a desired shape is secured to a tip part of an operation wire inserted through a sheath.

For example, Japanese Unexamined Patent Application, First Publication No. 2000-271146 discloses an example in which the treatment device for endoscope is a high-frequency snare. In this treatment device for endoscope, both end parts of a loop wire (elastic wire) formed in a loop shape are connected by substantially cylindrical connection pipes (connecting members) to the tip part of an operation wire.

Japanese Unexamined Patent Application, First Publication No. H11-285500 discloses an example in which the treatment device for endoscope is a basket-shaped gripper. In this treatment device for endoscope, four wires constitute one group, with a front end and a rear end of each wire being bound to a respective front-end chip and a respective rear-end chip. A front tip part of the operation wire is then secured to the rear-end chip, whereby the group of four wires forms a basket part for gripping.

SUMMARY OF THE INVENTION

According to a first aspect of the invention, a treatment device for endoscope includes: a flexible sheath, an operation wire that is advanceably/retreatably inserted into the sheath, a treatment part comprising at least one elastic wires that is capable of entering and exiting a tip side inner part of the sheath, and a connecting member that secures to each other a tip of the operation wire and ends of the elastic wires. The connecting member includes a cylindrical body part, and a plurality of walls that extend from one end face of the body unit in the direction of the axis of the body unit, a proximal end of the operation wire being secured to the body unit, and the plurality of ends of the elastic wires are secured to the wall in the direction of the axis; when viewed from the wall side in the direction of the axis, at least one of the ends of the elastic wires overlaps with the body unit. The interval between mutually adjacent walls is narrower than the outer diameter of the elastic wires.

In the treatment device for endoscope, the interval between adjacent walls is preferably smaller than the outer diameter of the elastic wires.

In the treatment device for endoscope, a pair of the walls is preferably formed with the axis of the body unit as their axis of line symmetry.

Preferably, in the treatment device for endoscope, one elastic wire is provided and is formed in a loop shape, and both ends of this elastic wire are secured to the connecting member.

Preferably, in the treatment device for endoscope, two elastic wires are provided. The proximal ends of the elastic wires are connected together to form a loop shape, and the distal ends are connected to the connecting member.

Preferably, in the treatment device for endoscope, three or more the elastic wires are provided, a distal end of each elastic wire is connected to a distal end of at least one other elastic wire, and proximal ends of the elastic wires are each secured to the connecting member; the treatment part is formed as a basket-shaped gripping instrument.

Preferably, in the treatment device for endoscope, two elastic wires are provided, distal ends of the elastic wires are formed such that they open at a predetermined angle to each other, and proximal ends of the elastic wires are each secured to the connecting member; the treatment part is formed as a two-legged forceps.

DETAILED DESCRIPTION OF THE INVENTION

First Embodiment

A first embodiment of a treatment device for endoscope according to the present invention will be explained with reference to FIG. 1 to FIG. 6, taking as an example a case where the treatment device for endoscope is a high-frequency snare.

Figure 1:
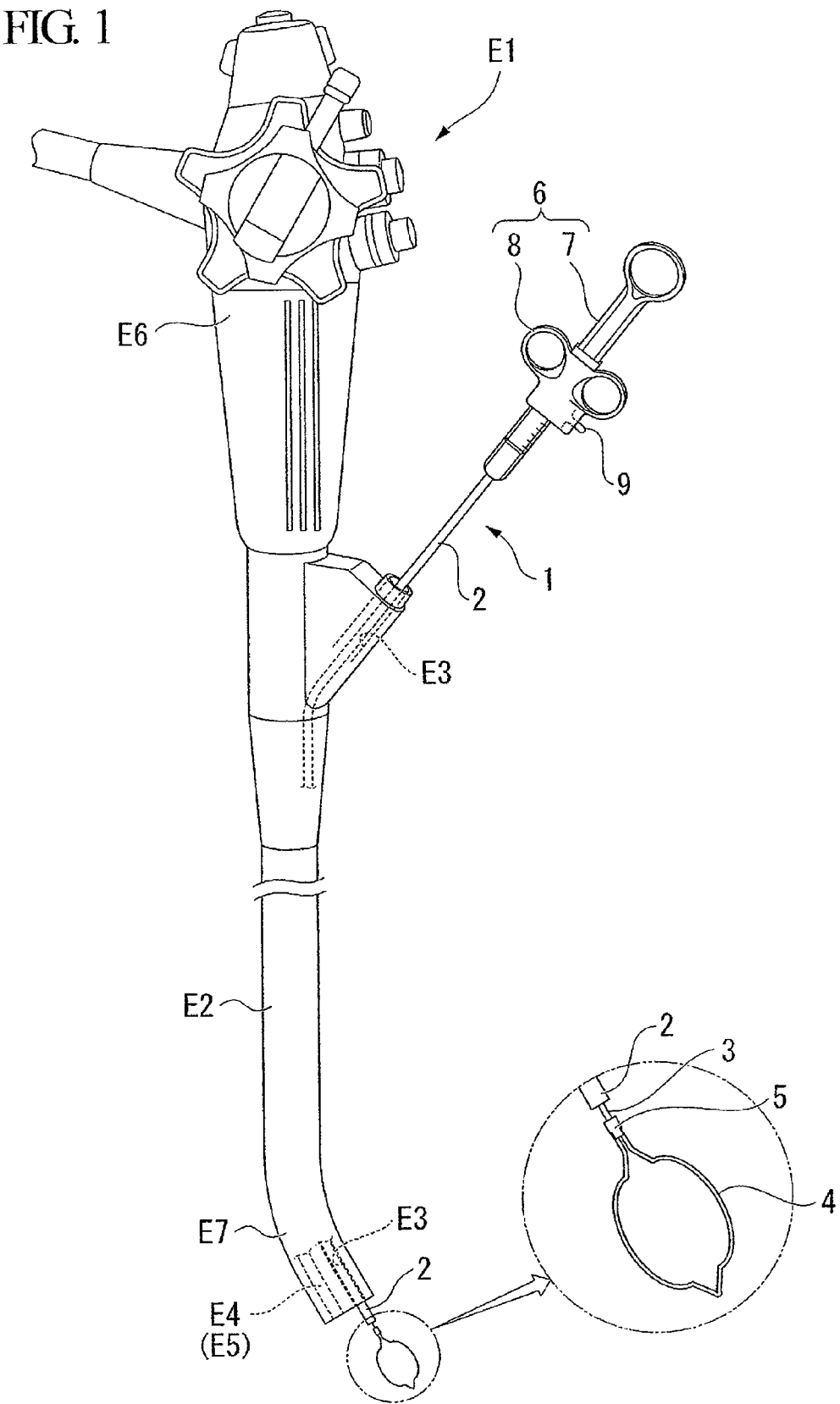
FIG. 1 is a schematic view of a state where a high-frequency snare of a first embodiment of the present invention is attached to an endoscope.

As shown in FIG. 1, a high-frequency snare 1 is a treatment device that is attached to an endoscope E1 by inserting into a work channel E3 formed in an elongated insertion part E2 of the endoscope E1.

An illumination mechanism E4 that radiates illumination light to the front, and an observation mechanism E5 that detects light, are each provided in an exposed state on a distal end face of the insertion part E2. Light detected by the observation mechanism E5 can be displayed on a display part (not shown).

By operating an endoscope operation part E6 connected to the proximal end side of the insertion part E2, a bendable part E7 provided on the distal end side of the insertion part E2 can be operated, and so can the illumination mechanism E4 and the observation mechanism E5.

The high-frequency snare 1 includes a flexible sheath 2, an operation wire 3 that is advanceably/retreatably inserted into the sheath 2, a loop-shaped snare wire (treatment part) 4 that is capable of entering and exiting a tip side inner part of the sheath 2, and a connecting member 5 that secures to each other the tip of the operation wire 3 and both ends of the snare wire 4. The high-frequency snare 1 of this embodiment further includes a snare operation part 6 provided at the proximal end of the sheath 2.

In this embodiment, the snare wire 4 is formed in a loop shape from a single elastic wire, and both ends of this elastic wire are secured to the connecting member 5.

The snare operation part 6 includes an operation part body 7 connected to the proximal end of the sheath 2, and a slider 8 that can advance and retreat with respect to the operation part body 7. The slider 8 is also provided with an electrode terminal 9 that connects to a high-frequency power source (not shown).

The slider 8 is connected to the proximal end of the operation wire 3. The operation wire 3 is electrically connected to the electrode terminal 9. The connecting member 5 is formed from a metal of, for example, copper or stainless steel. The operation wire 3 and the snare wire 4 are electrically connected via the connecting member 5.

Figure 2:
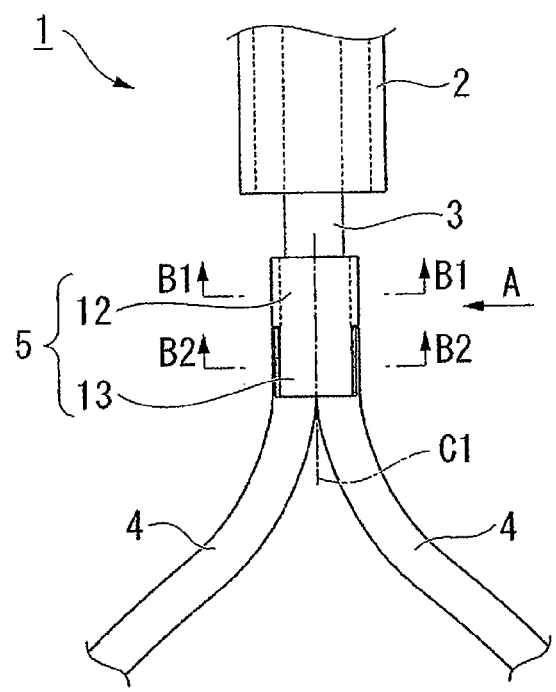
FIG. 2 is an enlarged view of the essential parts of the high-frequency snare of FIG. 1.
Figure 3:
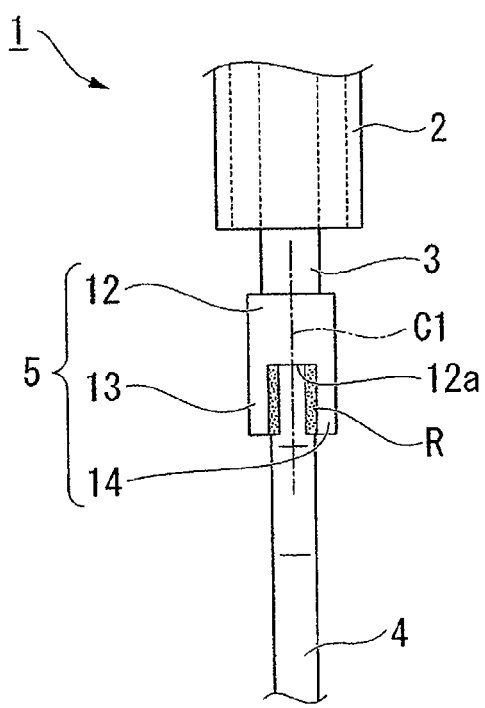
FIG. 3 is a view in the direction A of the arrow in FIG. 2.

As shown in FIG. 2 and FIG. 3, the connecting member 5 includes a cylindrical body part 12, and a pair of walls 13 and 14 that extend in the direction of the axis C1 of the body part 12 from one end face 12a thereof.

Figure 5:
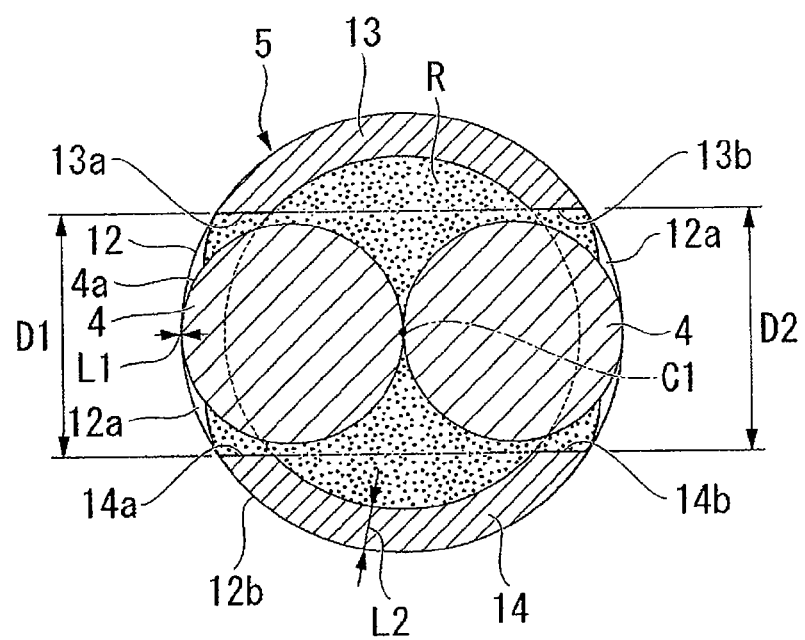
FIG. 5 is a cross-sectional view taken along cutoff line B2-B2 in FIG. 2.

As shown in FIG. 5, the walls 13 and 14 are formed with the axis C1 as their axis of line symmetry, and are substantially C-shaped when viewed in the direction of the axis C1. End faces 13a and 13b of the wall 13 are formed in the same plane, and so are end faces 14a and 14b of the wall 14. An interval D1 between end face 13a and end face 14a, and an interval D2 between end face 13b and end face 14b, are configured to be equal, and both gaps D1 and D2 are configured to be larger than the outer diameter of the snare wire 4. In this embodiment, the outer diameter of the body part 12 is set at twice the outer diameter of the snare wire 4.

Figure 4:
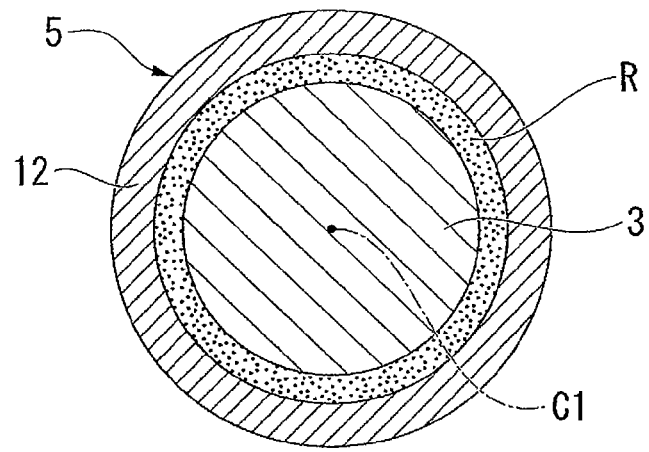
FIG. 4 is a cross-sectional view taken along cutoff line B1-B1 in FIG. 2.

As shown in FIG. 4, the tip of the operation wire 3 is arranged substantially in the same axis as the body part 12 of the connecting member 5, and is secured to the inner peripheral face of the body part 12 by, for example, soldering with a solder R. The method of securing the tip of the operation wire 3 to the body part 12 is not limited to soldering, and can instead be accomplished using brazing, swaging, laser welding, spot welding, etc.

As shown in FIGS. 2 and 5, both ends of the snare wire 4 are arranged between the walls 13 and 14 such that they are in close contact with each other in the direction of the axis C1. Moreover, when viewed in the direction of the axis C1 from the walls 13 and 14 sides, both ends of the snare wire 4 overlap the end face 12a of the body part 12.

Like the tips of the operation wire 3 described above, both ends of the snare wire 4 are secured to the walls 13 and 14 by, for example, soldering with a solder R.

Subsequently, a procedure will be explained whereby endoscope E1 with the high-frequency snare 1 attached thereto as in the configuration described above is used in excising a target tissue in a body.

Firstly, the user operates the endoscope operation part E6 of the endoscope E1 to irradiate illuminating light from the illumination mechanism E4 to the front of the insertion part E2, and causes the light detected by the observation mechanism E5 to be displayed as an image on the display unit. The high-frequency snare 1 is not attached to the endoscope E1 at this time.

Figure 6:
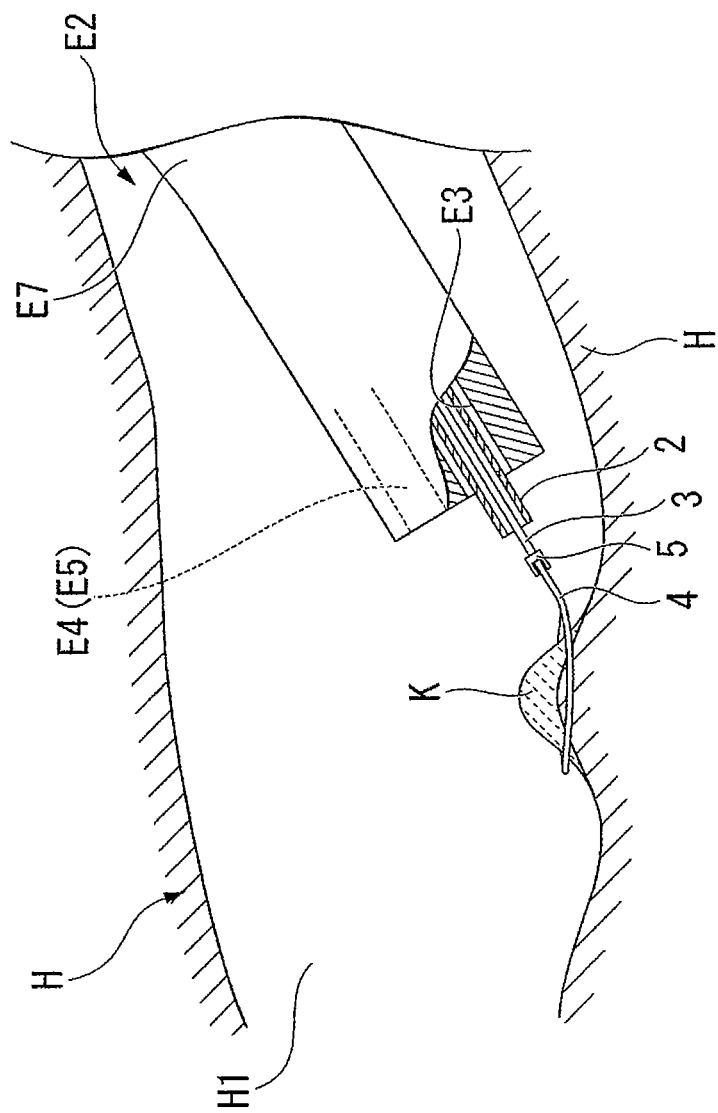
FIG. 6 is an explanatory diagram of a sequence for excising a target tissue in a body using an endoscope which a high-frequency snare is attached to in a first embodiment of the present invention.

While confirming the image displayed on the display unit, the user operates the endoscope operation part E6 to make the bendable part E7 bend, and, as shown in FIG. 6, inserts the insertion part E2 into a body cavity P1 of an examinee P. When the target tissue K in front of the insertion part E2 is confirmed on the display unit, the position of the tip of the insertion part E2 is secured.

Outside the examinee P, the slider 8 is pulled with respect to the operation part body 7 so that the snare wire 4 is stored inside the sheath 2.

Then the sheath 2 of the high-frequency snare 1 is inserted through the work channel E3 of the endoscope E1, and leads the tip of the sheath 2 of the high-frequency snare 1 to the vicinity of the target tissue K.

Then the slider 8 is pushed with respect to the operation part body 7, such that the snare wire 4 slowly opens into a loop shape at the tip of the sheath 2. Then the endoscope E1 is operated and encloses the target tissue K within the loop-shaped snare wire 4.

Then the slider 8 is pulled with respect to the operation part body 7, and binds the base of the target tissue K with the snare wire 4. A high-frequency current from the high-frequency power source (not shown) flows through the snare wire 4, burning the base of the target tissue K and thereby excising it.

Thus, in the high-frequency snare 1 of the first embodiment of the present invention, both ends of the snare wire 4 are secured to the walls 13 and 14 of the connecting member 5 in the direction of the axis C1, and overlap with the end face 12a of the body part 12 when viewed in the direction of the axis C1 from the walls 13 and 14 side.

Consequently, as shown in FIG. 5, viewed in the direction of the axis C1, the distance L1 from an outer peripheral surface 4a of the snare wire 4 to an outer peripheral surface 12b of the body part 12 can be made shorter than the distance L2 that constitutes the thickness of the body part. In this embodiment, the distance L1 is 0.

Therefore, in comparison with a case where the connecting member 5 is secured by simply fitting both ends of the snare wire 4 from the outer periphery and grasping, the outer diameter of the connecting member 5 required for securing both ends of the snare wire 4 can be reduced.

Moreover, when the outer diameter of the connecting member 5 is reduced, it also becomes possible to reduce the outer diameter of the sheath 2 of the high-frequency snare 1 and the outer diameter of the insertion part E2 of the endoscope E1.

The pair of walls 13 and 14 are formed with the direction of the axis C1 as their axis of line symmetry. This enables both ends of the snare wire 4 to overlap the end faces 12a of the body part 12. Therefore, both ends of the snare wire 4 can be secured with a connecting member 5 having a smaller outer diameter.

Furthermore, the end faces 13a and 13b of the wall 13 are formed in the same plane, and so are the end faces 14a and 14b of the wall 14; in addition, the gaps D1 and D2 are configured to be equal. Therefore, the walls 13 and 14 can be formed by a single cutting away of a cylindrical member, making them easier to process.

Instead of the connecting member 5 of this embodiment, connecting members shown in FIGS. 7 to 10 may be used. In the following modifications, like parts to those of the connecting member 5 of this embodiment are designated with like reference numerals and are not repetitiously explained; only points of difference will be explained.

Figure 7:
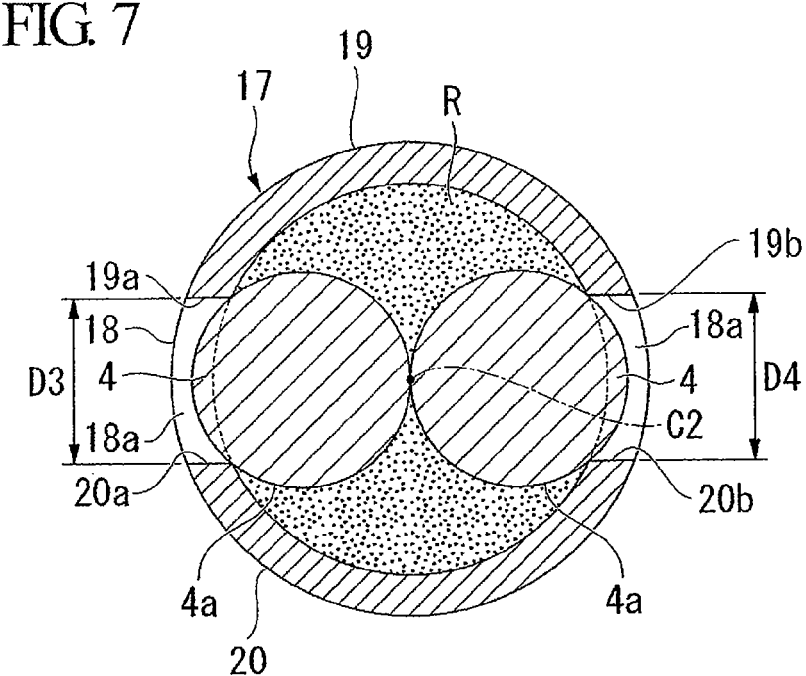
FIG. 7 is a cross-sectional view of the essential parts of a modification of a connecting member of a high-frequency snare in a first embodiment of the present invention.

As shown in FIG. 7, a connecting member 17 includes a cylindrical body part 18, and a pair of walls 19 and 20 that extend in the direction of the axis C2 of the body part 18 from one end face 18a thereof. The outer diameter of the body part 18 is greater than the outer diameter of the body part 12 of the embodiment described above.

The walls 19 and 20 are formed with the axis C2 as their axis of line symmetry, and are substantially C-shaped when viewed in the direction of the axis C2. End faces 19a and 19b of the wall 19 are formed in the same plane, and so are end faces 20a and 20b of the wall 20. An interval D3 between end face 19a and end face 20a, and an interval D4 between end face 19b and end face 20b, are configured to be equal, and both gaps D3 and D4 are configured to be smaller than the outer diameter of the snare wire 4.

When the high-frequency snare 1 is provided with the connecting member 17 having this configuration, the ends of the snare wire 4 are prevented from slipping out from the walls 19 and 20 in the direction of the diameter of the body part 18. The ends of the snare wire 4 can thus be secured more reliably by the connecting member 17.

Figure 8:
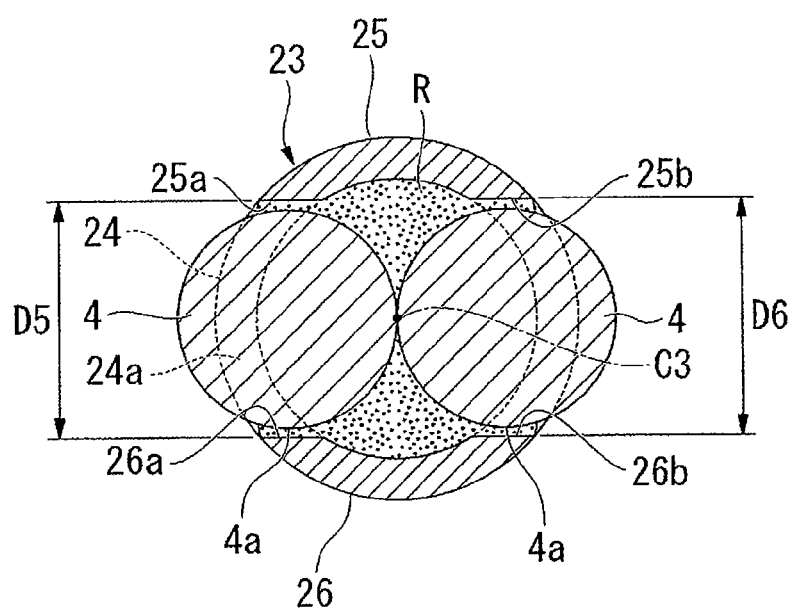
FIG. 8 is a cross-sectional view of the essential parts of a modification of a connecting member of a high-frequency snare in a first embodiment of the present invention.

The connecting member 23 shown in FIG. 8 includes a cylindrical body part 24, and a pair of walls 25 and 26 that extend in the direction of the axis C3 of the body part 24 from one end face 24a thereof. The outer diameter of the body part 24 is configured to be smaller than the outer diameter of the body part 12 of the embodiment described above.

The pair of walls 25 and 26 are formed with the axis C3 as their axis of line symmetry, and are substantially C-shaped when viewed in the direction of the axis C3. End faces 25a and 25b of the wall 25 are formed in the same plane, and so are end faces 26a and 26b of the wall 26. An interval D5 between end face 25a and end face 26a, and an interval D6 between end face 25b and end face 26b, are configured to be equal, and both gaps D5 and D6 are configured to be greater than the outer diameter of the snare wire 4.

Figure 9:
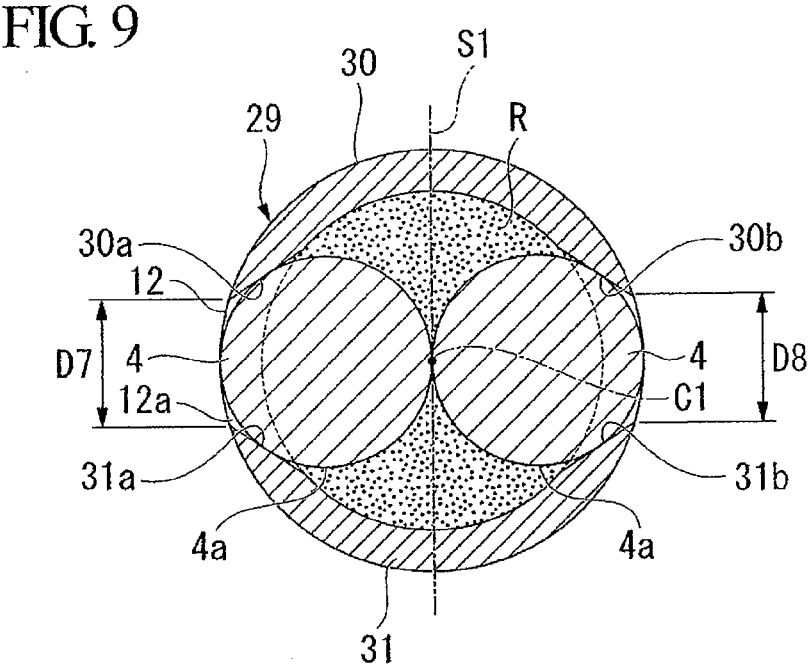
FIG. 9 is a cross-sectional view of the essential parts of a modification of a connecting member of a high-frequency snare in a first embodiment of the present invention.

The connecting member 29 shown in FIG. 9 includes the body part 12, and a pair of walls 30 and 31 that extend in the direction of the axis C1 of the body part 12 from one end face 12a thereof.

The walls 30 and 31 are substantially C-shaped when viewed in the direction of the axis C1. The walls 30 and 31 are formed with the direction of the axis C1 as their axis of line symmetry, and each is asymmetrical to an imaginary plane S1 contacting each of them to the outer peripheral surface 4a of the snare wire 4.

Moreover, an end face 30a of the wall 30 and an end face 31a of the wall 31 are each formed on a predetermined plane, the distance between the end face 30a and the end face 31a becoming smaller with a distance away from the axis C1. Similarly, an end face 30b of the wall 30 and an end face 31b of the wall 31 are each formed on a predetermined plane, the distance between the end face 30b and the end face 31b becoming smaller with a distance away from the axis C1.

An interval D7 between the end face 30a and the end face 31a, and an interval D8 between the end face 30b and the end face 31b, are configured to be equal, and both gaps D7 and D8 are configured to be smaller than the outer diameter of the snare wire 4.

When the high-frequency snare 1 is provided with the connecting member 29 having this configuration, the ends of the snare wire 4 are prevented from slipping out from the walls 30 and 31 in the direction of the diameter of the body part 12. Both ends of the snare wire 4 can thus be secured more reliably by the connecting member 29. Furthermore, even when the ends of the snare wire 4 are prevented from slipping out in the direction of the diameter of the body part 12, the outer diameter of the connecting member 29 can be made small in comparison with the outer diameter of the connecting member 17 in the modification described above.

Figure 10:
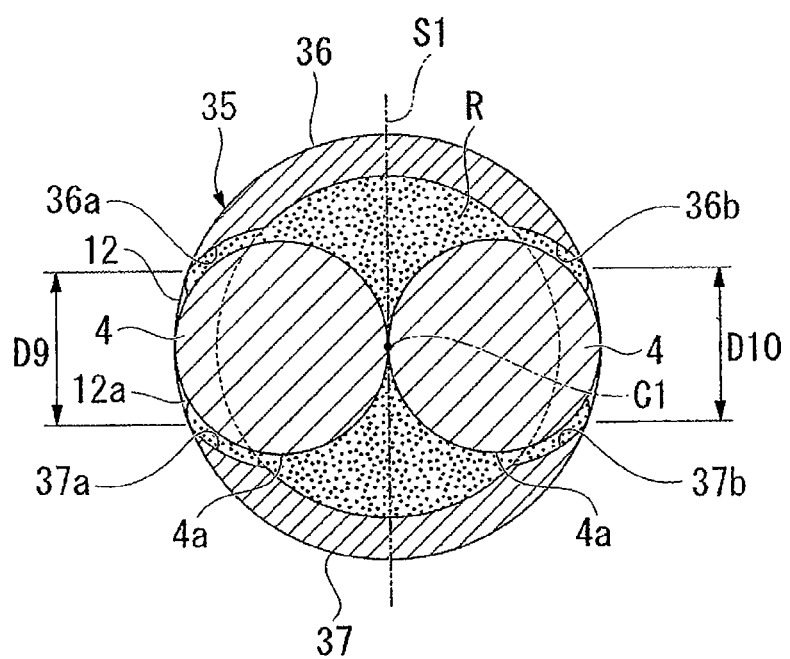
FIG. 10 is a cross-sectional view of the essential parts of a modification of a connecting member of a high-frequency snare in a first embodiment of the present invention.

The connecting member 35 shown in FIG. 10 includes a body part 12, and a pair of walls 36 and 37 that extend in the direction of the axis C1 of the body part 12 from one end face 12a thereof.

The walls 36 and 37 are substantially C-shaped when viewed in the direction of the axis C1. The walls 36 and 37 are formed with the direction of the axis C1 as their axis of line symmetry, and each is asymmetrical to the imaginary plane S1.

An end face 36a of the wall 36 and an end face 37a of the wall 37 are separated by a predetermined distance from the outer peripheral surface 4a of the end of one snare wire 4, and each is coaxial with the outer peripheral surface 4a of that snare wire 4. Similarly, an end face 36b of the wall 36 and an end face 37b of the wall 37 are separated by a predetermined distance from the outer peripheral surface 4a of the end of the other snare wire 4, and each is coaxial with the outer peripheral surface 4a of that snare wire 4.

An interval D9 between end face 36a and end face 37a, and an interval D10 between end face 36b and end face 37b, are configured to be equal, and both gaps D9 and D10 are configured to be smaller than the outer diameter of the snare wire 4.

When the high-frequency snare 1 is provided with the connecting member 35 having this configuration, the ends of the snare wire 4 are prevented from slipping out from the walls 36 and 37 in the direction of the diameter of the body part 12. The ends of the snare wire 4 can thus be secured more reliably by the connecting member 35. Furthermore, even when the ends of the snare wire 4 are prevented from slipping out in the direction of the diameter of the body part 12, the outer diameter of the connecting member 35 can be made small in comparison with the outer diameter of the connecting member 17 in the modification described above.

Second Embodiment

Subsequently, a second embodiment of the present invention will be explained. Like parts to those of the embodiment described above are designated with like reference numerals and are not repetitiously explained; only points of difference will be explained.

Figure 11:
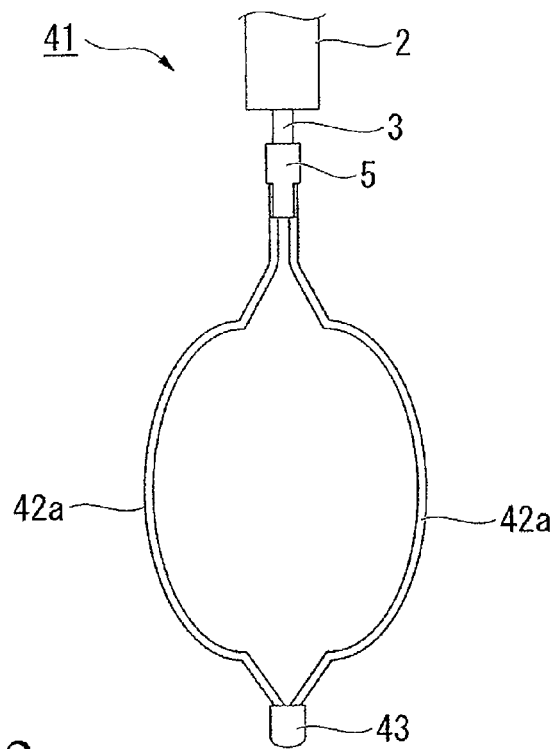
FIG. 11 is an enlarged view of the essential parts of a modification of a connecting member of a high-frequency snare in a second embodiment of the present invention.

As shown in FIG. 11, a high-frequency snare (treatment device for endoscope) 41 of this embodiment includes a snare wire 42 instead of the snare wire 4 of the high-frequency snare 1 of the embodiment described above. The snare wire 42 is configured such that distal ends of two looped wires (elastic wires) 42a and 42b are connected together by a distal chip 43, forming a loop shape. Proximal ends of the looped wires (elastic wires) 42a and 42b are secured to a connecting member 5.

According to the high-frequency snare 41 having this configuration, similar effects to those of the embodiment described above can be obtained.

Third Embodiment

Subsequently, a third embodiment of the present invention will be explained. Like parts to those of the embodiments described above are designated with like reference numerals and are not repetitiously explained; only points of difference will be explained.

Figure 12:
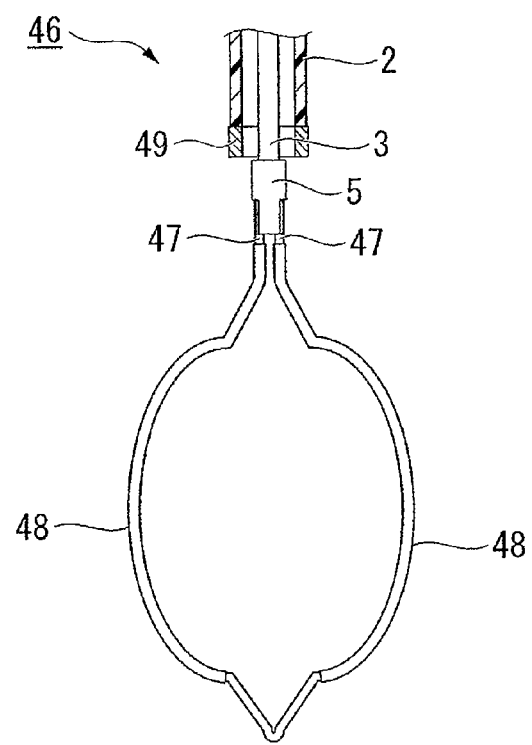
FIG. 12 is an enlarged view of the essential parts of a fractured section of a high-frequency snare in a third embodiment of the present invention.

As shown in FIG. 12, a high-frequency snare (treatment device for endoscope) 46 of this embodiment includes, instead of the snare wire 4 of the high-frequency snare 1 of the embodiment described above, a high-impedance snare wire 47 made of, for example, nichrome wire. The snare wire 47 is formed in a loop shape, and a range from the portion secured to the connecting member 5 to the portion exposing the tip of the snare wire 47 is covered by a pair of insulating coatings 48. A sheath tip passive electrode 49 is provided at the tip of the sheath 2.

According to the high-frequency snare 46 having this configuration, when an electrical current is passed through the snare wire 47, the snare wire 47 generates heat. The insulating covers 48 covering the snare wire 47 are heated to a level at which they can coagulate the tissue. Due to the concentration of current which is similar to that in a conventional high-frequency snare, the distal end of the snare wire 47 that is not covered by the insulating covers 48 is heated to a level that can cut the tissue. Thus, after the insulating covers 48 have coagulated the tissue and stopped bleeding, the distal end of the snare wire 47 can cut the tissue.

Therefore, the tissue can be speedily cut while suppressing bleeding.

Fourth Embodiment

Subsequently, a fourth embodiment of the present invention will be explained. Like parts to those of the embodiments described above are designated with like reference numerals and are not repetitiously explained; only points of difference will be explained.

Figure 13:
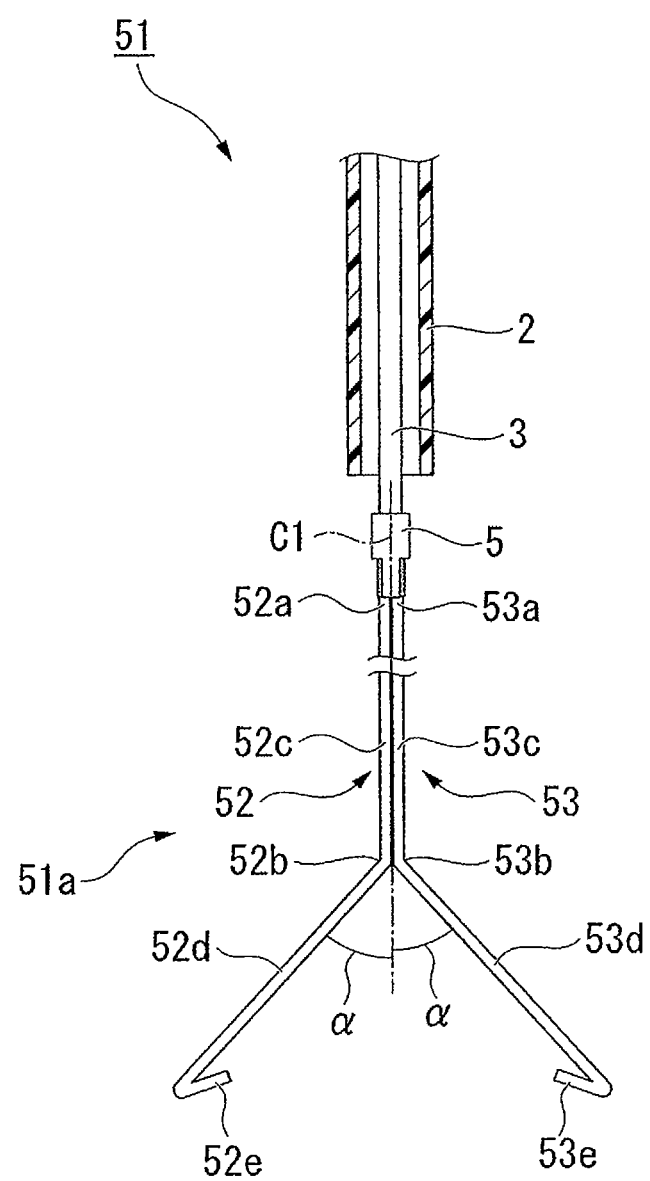
FIG. 13 is an enlarged view of the essential parts of a fractured section of a part of a two-legged forceps in a fourth embodiment of the present invention.

As shown in FIG. 13, a two-legged forceps (treatment device for endoscope) 51 of this embodiment includes, instead of the snare wire 4 of the high-frequency snare 1 in the embodiment described above, a treatment part 51a including legs 52 and 53 formed from elastic wires.

The legs 52 and 53 respectively include connecting parts 52a and 53a that are provided at the proximal end thereof and secured to the connecting member 5, curved parts 52b and 53b that are arranged on the distal end side of the connecting parts 52a and 53a and whose distal end sides are curved with respect to the axis C1 such that they open at a predetermined angle α to each other, parallel parts 52c and 53c that are disposed between the connecting parts 52a and 53a and the curved parts 52b and 53b with a constant interval between the legs 52 and 53, straight parts 52d and 53d that extend in a straight line from the curved parts 52b and 53b toward the distal end side while maintaining the angle α, and distal end gripping parts 52e and 53e that are provided at the distal ends of the straight parts 52d and 53d and grip the target tissue.

According to the two-legged forceps 51 having this configuration, in the state shown in FIG. 13, when the target tissue is gripped between the distal end gripping parts 52e and 53e and the operation wire 3 is pulled, the straight parts 52d and 53d are pressed by the inner peripheral face of the sheath 2, reducing the interval between the straight parts 52d and 53d. A high-frequency current from a high-frequency power source (not shown) is then fed through the operation wire 3 into the legs 52 and 53, thereby burning and cutting the tissue between the distal end gripping parts 52e and 53e.

Fifth Embodiment

Subsequently, a fifth embodiment of the present invention will be explained. Like parts to those of the embodiments described above are designated with like reference numerals and are not repetitiously explained; only points of difference will be explained.

Figure 14:
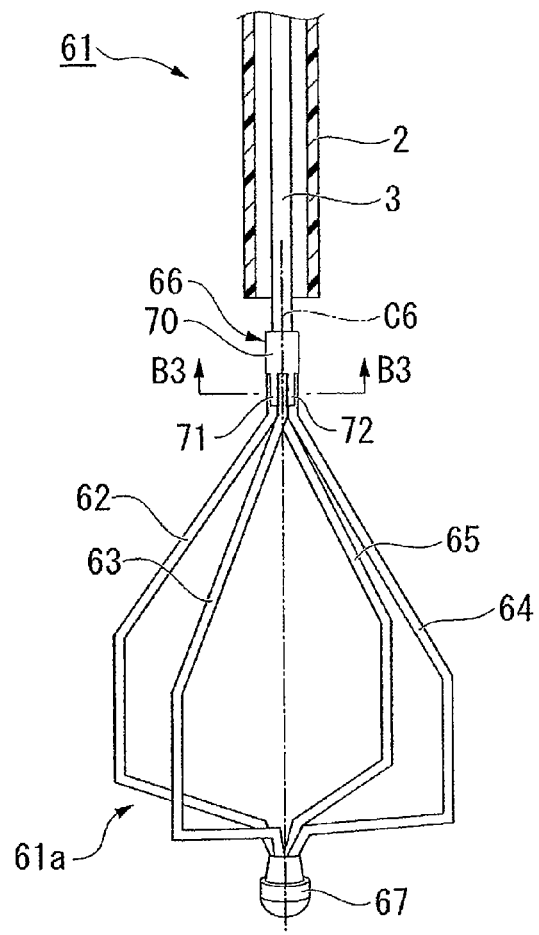
FIG. 14 is an enlarged view of the essential parts of a fractured section of a part of a basket-shaped gripper in a fifth embodiment of the invention.

As shown in FIG. 14, a basket-shaped gripping instrument (treatment device for endoscope) 61 of this embodiment includes, instead of the snare wire 4 of the high-frequency snare 1, a treatment part 61a which is provided with four elastic wires 62 to 65.

The proximal end of each of the elastic wires 62 to 65 is secured via a connecting member 66 to the distal end of the operation wire 3, and the distal end is secured to a distal chip 67 provided on the axis C6 of the operation wire 3 on the distal end side thereof. The elastic wires 62 to 65 are arranged at equal angles around the axis C6, and bend into a shape that leads away from the axis C6 such as to form a predetermined space within them.

Figure 15:
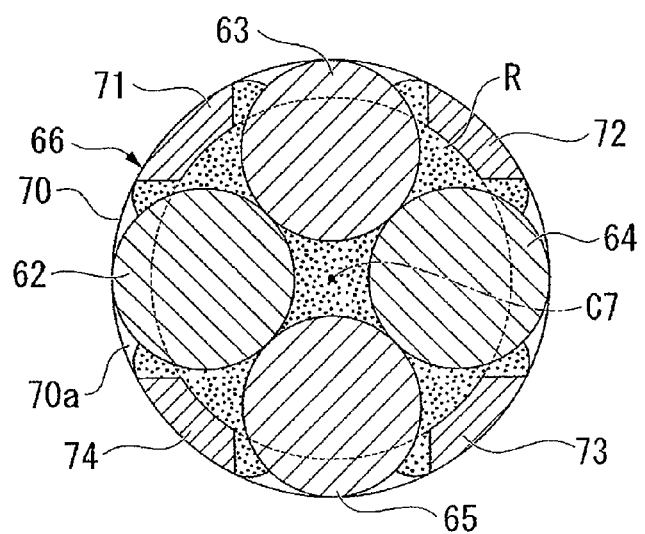
FIG. 15 is a cross-sectional view taken along the cutoff line B3-B3 in FIG. 14.

As shown in FIG. 14 and FIG. 15, the connecting member 66 includes a cylindrical body part 70, and walls 71 to 74 that extend from one end face 70a of the body part 70 in the direction of the axis C7 of the body part 70. The walls 71 to 74 are arranged at equal angles around the axis C7.

The proximal end of the operation wire 3 is arranged substantially coaxial to the body part 70 of the connecting member 66, and is secured to the body part 70 by, for example, soldering.

Distal ends of the elastic wires 62 to 65 are arranged such that they are in close contact with each other in the direction of the axis C7. Moreover, when viewed in the direction of the axis C7 from the walls 71 and 74 sides, the distal ends of elastic wires 62 to 65 overlap the end face 70a of the body part 70.

As with the proximal end of the operation wire 3 described above, the distal ends of the elastic wires 62 to 65 are secured to the walls 71 to 74 respectively by, for example, soldering with a solder R.

In the state shown in FIG. 14, the basket-shaped gripping instrument 61 having this configuration captures a stone (not shown) in the treatment part 61a. When the operation wire 3 is pulled, the treatment part 61a compresses, whereby the stone is reliably grasped inside the treatment part 61a.

The basket-shaped gripping instrument 61 is then extracted from the body cavity together with the endoscope E1, and the stone is collected.

In the basket-shaped gripping instrument 61 of this embodiment, the treatment part 61a includes four elastic wires 62 to 65. However, there is no limitation on the number of elastic wires constituting the treatment device; any number may be used, three being the minimum.

While the first to the fifth embodiments of the invention have been described and illustrated above, it should be understood that there are no limitations on the specific configuration. Various modifications can be made to the configuration without departing from the spirit or scope of the invention.

For example, in the first to the fifth embodiments described above, when viewed in the direction of the axis from the wall side, all ends of the elastic wires overlap the end face of the body part. However, this should not be considered limitative, and any number of ends of the elastic wires may overlap the end face of the body part 12, the minimum being one.

Furthermore, the connecting member in the first to the fifth embodiments of the invention may have any number of walls, the minimum being one.

Furthermore, in the first to the fifth embodiments of the present invention, the body part of the connecting member is cylindrical. However, the body part of the connecting member is not limited to this shape, and may have a hollow elliptical shape, a hollow rectangular shape, or the like, when view from the direction of the axis of the connecting member.

Furthermore, walls having various configurations may be used as the wall of the connecting member in the second to fifth embodiments of the present invention, such as the wall described in the first embodiment and the modifications thereof.

What is claimed is:

1. A treatment device for an endoscope comprising:
    a flexible sheath;
    an operation wire that is advanceably/retreatably inserted into the sheath,
    a treatment part comprising at least one elastic wire that is capable of entering and exiting a tip side inner part of the sheath; and
    a connecting member that secures to each other a tip of the operation wire and ends of the elastic wire; wherein
    the connecting member includes a cylindrical body part, and a plurality of mutually adjacent walls that extend from one end face of the body part in the direction of the axis of the body part;
    a distal end of the operation wire is fixed to the body part;
    the ends of the elastic wire are fixed to the wall in the direction of the axis;
    an interval between the mutually adjacent walls is configured to be narrower than the outer diameter of the elastic wire,
    when viewed from in the direction of the axis of the connecting member, at least one of the ends of the elastic wire fixed to the wall overlaps with the one end face of the body part, and at least a portion of the end is beyond the inner periphery of the body part in the radial direction to the outside.

2. The treatment device for the endoscope according to claim 1, wherein a pair of the walls are formed with the axis of the body part as their axis of line symmetry.

3. The treatment device for the endoscope according to claim 1, wherein one elastic wire is provided and is formed in a loop shape.

4. The treatment device for the endoscope according to claim 1, wherein two elastic wires are provided,
    proximal ends of the elastic wires are connected together to form a loop shape, and the distal ends of the elastic wires are connected to the connecting member.

5. The treatment device for the endoscope according to claim 1, wherein three or more the elastic wires are provided;
    a distal end of each elastic wire is connected to a distal end of at least one other elastic wire;
    proximal ends of the elastic wires are each secured to the connecting member; and
    the treatment part is formed as a basket-shaped gripping instrument.

6. The treatment device for the endoscope according to claim 1, wherein two elastic wires are provided;
    distal ends of the elastic wires are formed such that they open at a predetermined angle to each other;
    proximal ends of the elastic wires are each secured to the connecting member; and
    the treatment part is formed as a two-legged forceps.

* * * * *